US012616378B2

(12) United States Patent
Geffe

(10) Patent No.: US 12,616,378 B2
(45) Date of Patent: May 5, 2026

(54) SENSOR DEVICE FOR ASCERTAINING INFLAMMATION-RELEVANT VITAL PARAMETERS

(71) Applicant: Markus Geffe, Duisburg (DE)

(72) Inventor: Markus Geffe, Duisburg (DE)

( * ) Notice: Subject to any disclaimer, the term of this patent is extended or adjusted under 35 U.S.C. 154(b) by 345 days.

(21) Appl. No.: 18/037,577

(22) PCT Filed: Nov. 18, 2021

(86) PCT No.: PCT/EP2021/082226
§ 371 (c)(1),
(2) Date: Aug. 18, 2023

(87) PCT Pub. No.: WO2022/106583
PCT Pub. Date: May 27, 2022

(65) Prior Publication Data
US 2024/0407651 A1      Dec. 12, 2024

(30) Foreign Application Priority Data

Nov. 20, 2020    (EP) .................................... 20209022

(51) Int. Cl.
A61B 5/01        (2006.01)
A61B 5/00        (2006.01)
G01K 13/20      (2021.01)
(52) U.S. Cl.
CPC ................ A61B 5/01 (2013.01); A61B 5/002 (2013.01); A61B 5/6826 (2013.01); G01K 13/20 (2021.01);
(Continued)
(58) Field of Classification Search
CPC ......... A61B 5/01; A61B 5/002; A61B 5/6826; A61B 2562/0271; A61B 2562/063;
(Continued)

(56) References Cited

U.S. PATENT DOCUMENTS 5,813,766 A      9/1998   Chen
6,846,106 B1 *   1/2005   Chen ........................ A61B 5/01
                                              340/407.1
(Continued)

FOREIGN PATENT DOCUMENTS

DE            29715113  U1    10/1997
DE      202006009103  U1    10/2006
(Continued)

OTHER PUBLICATIONS

Turk, "This sleep-tracking Oura ring can detect when you've drunk too much", Wired, 2019, 1-9.
(Continued)

*Primary Examiner* — Jonathan T Kuo
(74) *Attorney, Agent, or Firm* — CAHN & SAMUELS, LLP

(57) ABSTRACT

A sensor device for determining vital parameters relevant to inflammation includes a base body (1a) with a substantially rectangular base surface; an ring-shaped holder (2), which is fixed to the base body (1a), for placing on a finger of a patient; and at least one sensor arm (4), which is detachably fixed to the base body (1a). A sensor surface, which is functionally associated with a temperature sensor (6), is arranged at the end on the sensor arm (4) in such a way and the sensor arm (4) has such a length that the sensor surface in the position of use comes to rest on the base joint of the patient's finger. Means for storing and optionally transmitting the data measured by the temperature sensor to a data evaluation unit are provided in the base body, and the at least one sensor arm (4) fixed to the base body (1a) is detachably fixed to the base body.

17 Claims, 7 Drawing Sheets

(52) U.S. Cl.
CPC . *A61B 2562/0271* (2013.01); *A61B 2562/063*
(2013.01)

(58) Field of Classification Search
CPC ..... A61B 5/6843; A61B 5/0205; A61B 5/225;
A61B 5/4528; G01K 13/20; G01K 1/024;
G01K 1/14
See application file for complete search history.

(56) References Cited

U.S. PATENT DOCUMENTS

| | | | |
|---|---|---|---|
| 8,444,622 B2 | 5/2013 | Eckhoff et al. | |
| 9,335,790 B2 * | 5/2016 | Stotler | .................. G06F 1/1637 |
| 2008/0171915 A1 * | 7/2008 | Kawajiri | ............ A61B 5/14551 |
| | | | 600/300 |
| 2015/0133193 A1 * | 5/2015 | Stotler | ................ G06F 15/0216 |
| | | | 455/557 |
| 2018/0103868 A1 * | 4/2018 | Seko | ...................... A61B 5/681 |

FOREIGN PATENT DOCUMENTS

| | | | |
|---|---|---|---|
| EP | 2437039 A2 | 4/2012 |
| EP | 3075312 B1 | 7/2020 |
| WO | 2018073827 A1 | 4/2018 |

OTHER PUBLICATIONS

English Abstract for DE202006009103U1, Oct. 12, 2006.
Notification of Transmittal of Translation of the International Pre-
liminary Report of Patentability, May 25, 2023, 10 pages.

* cited by examiner

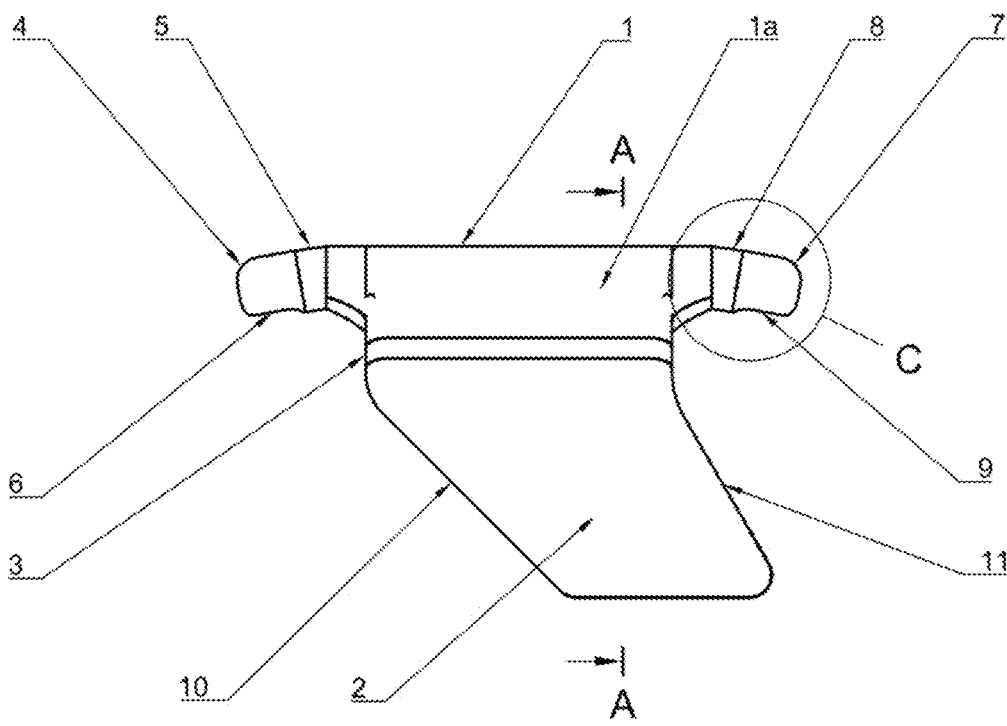
Figure 1
A-A (2:1)
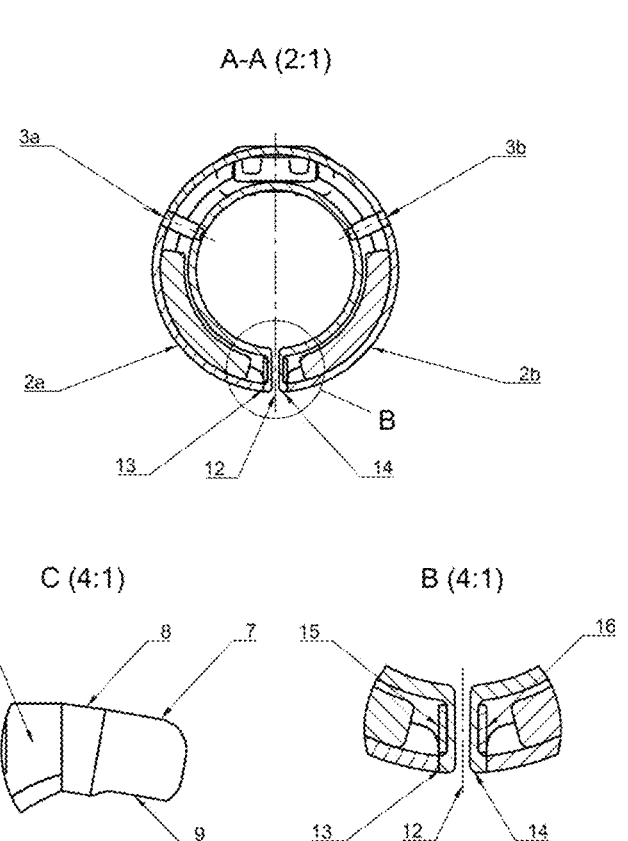
C (4:1)          B (4:1)
Figure 2A–C

D (4:1)

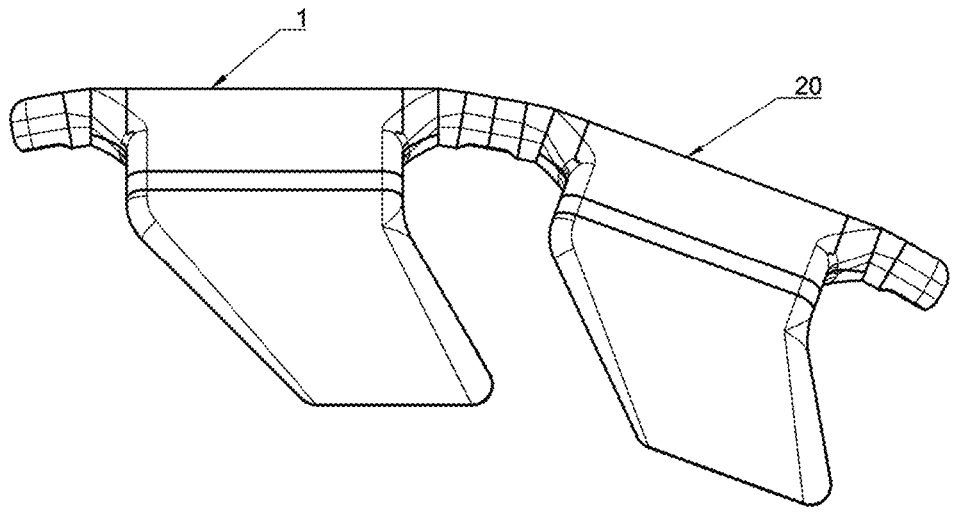
A
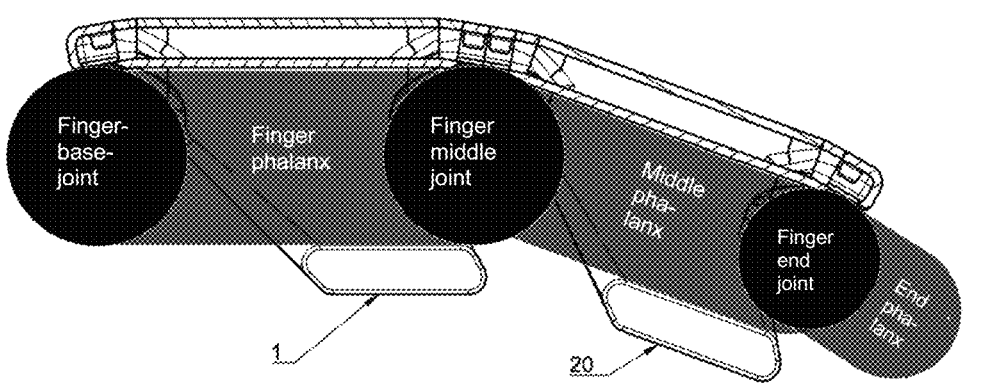
B
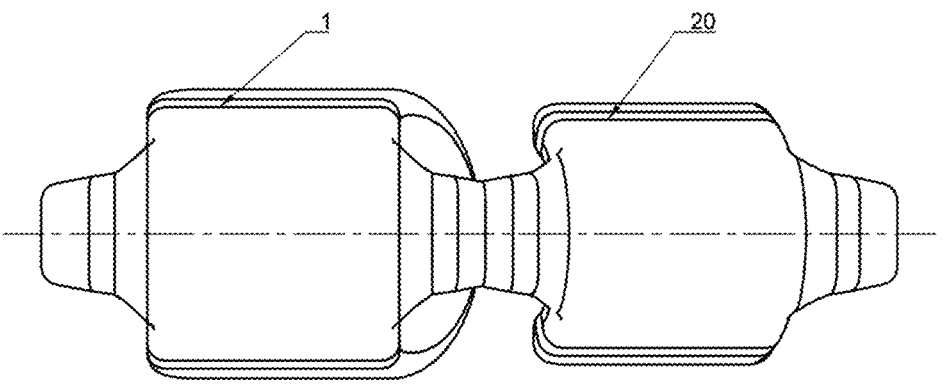
Figure 8 A-C

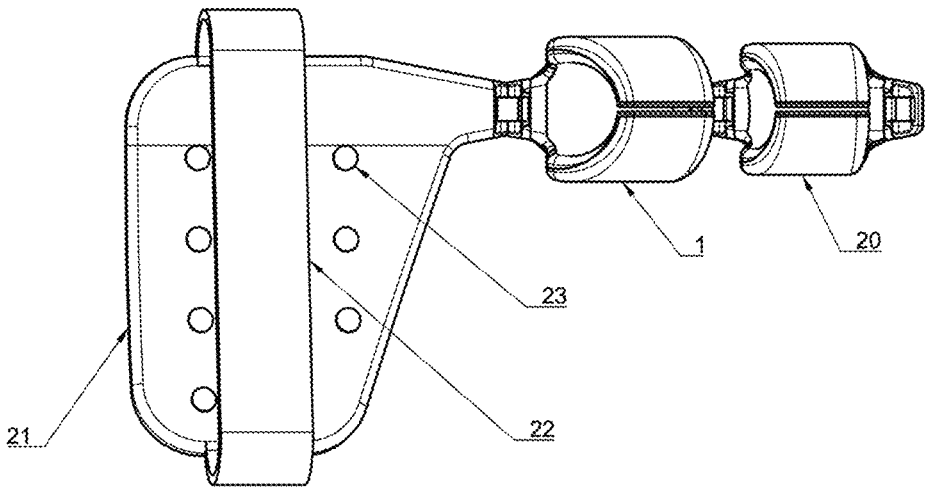
A
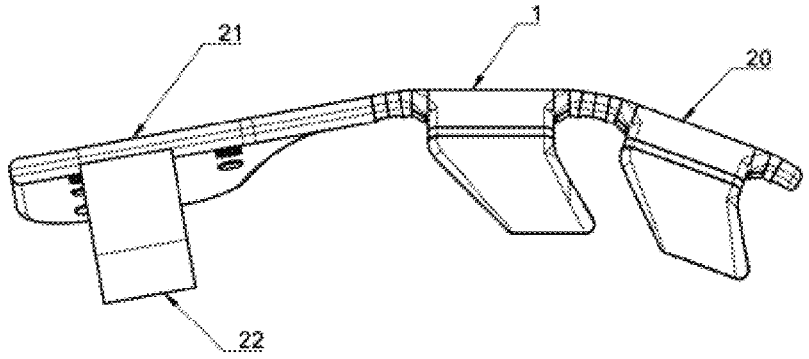
B
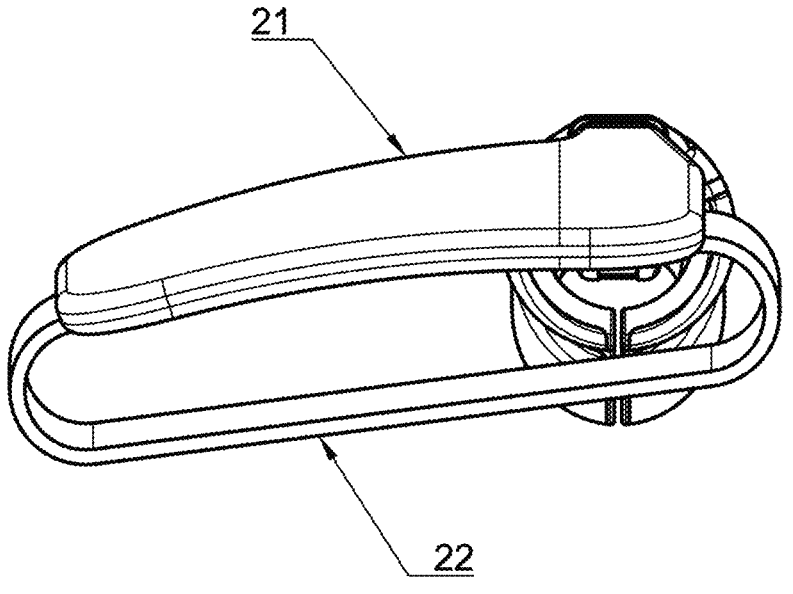
C
Figure 9 A-C

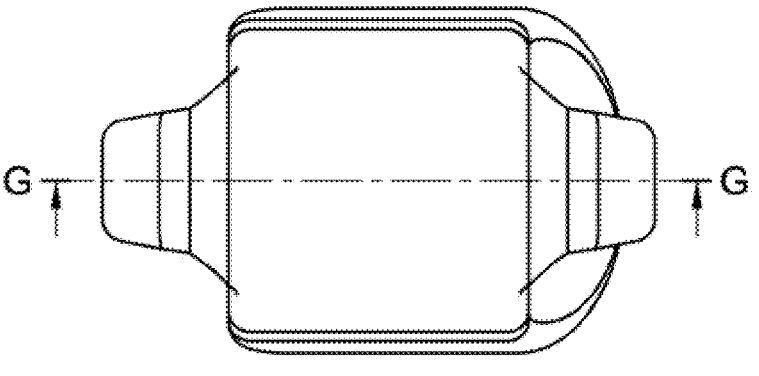
A
G – G
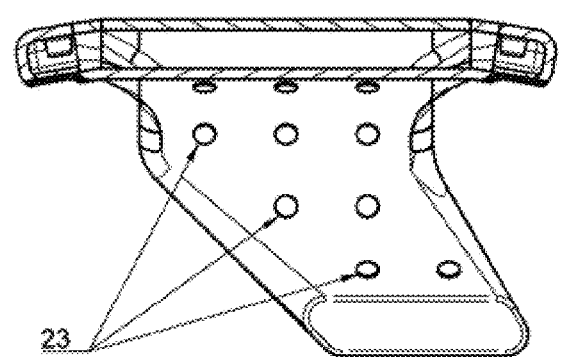
B
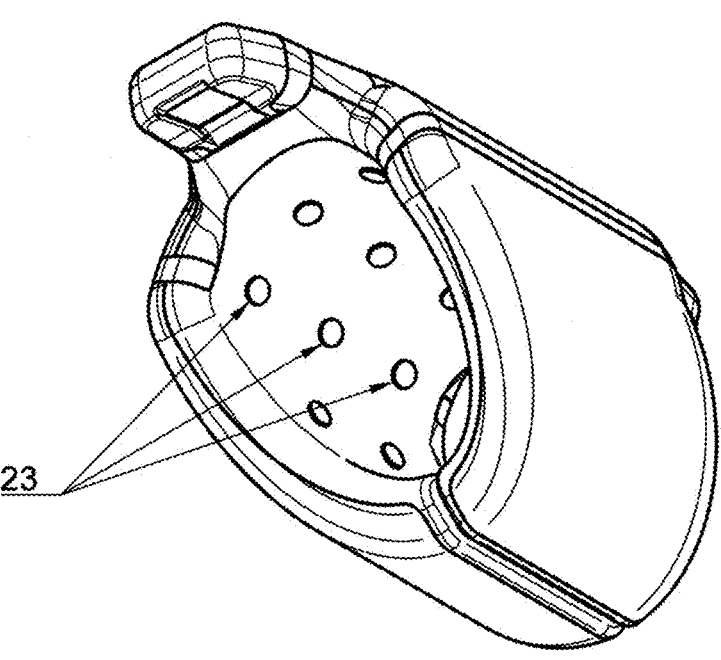
C
Figure 10 A-C

SENSOR DEVICE FOR ASCERTAINING INFLAMMATION-RELEVANT VITAL PARAMETERS

This U.S. patent application is a national stage application of PCT/EP2021/082226 filed on 18 Nov. 2021 and claims priority of European patent document EP 20209022.1 filed on 20 Nov. 2020, the entireties of which are incorporated herein by reference.

The present invention relates to a sensor device for determining vital parameters relevant to inflammation.

Inflammation is the body's own reaction to harmful stimuli, which is classically expressed by the signs of inflammation such as redness, swelling, pain and functional limitations. In this regard, messenger substances of the immune system cause the blood vessels to dilate, so that the area of inflammation is supplied with more blood and the vessels become more permeable for the escape of blood plasma and immune cells into the tissue. Any stimulus that exceeds the physiological level can trigger inflammation. This applies in particular to physical stimuli such as mechanical stimuli or foreign bodies such as metabolic products like uric acid crystals, as well as allergens and autoallergens, for example in rheumatic or autoimmune diseases.

Uric acid crystals are deposited, for example, in various peripheral joints and tissues as a result of a high uric acid concentration in the blood. Deposits of uric acid crystals lead to bone resorption near the joint and cartilage changes, which are reflected in the clinical picture of gouty arthritis. The joint is usually very red, extremely painful, very swollen and overheated.

Similar symptoms are observed in rheumatic diseases. Here, the body attacks its own structures such as the synovial membrane, for example in rheumatoid arthritis, and as a result of the mostly chronic inflammations, those affected by joint-related forms (articular rheumatism, or chronic articular rheumatism) suffer from pain, swelling or effusions of the joints and, as late consequences, from joint destruction, malpositions and loss of function.

The course of a rheumatic disease and the response to therapy can vary greatly from patient to patient, even with the same diagnosis. Timely diagnosis and therapy are often decisive for the course of a rheumatic disease in order to prevent the long-term consequences described above. To this end, it is particularly important to detect the first symptoms of a rheumatic disease or its flare-up in the affected joints at an early stage and to be able to initiate therapy in good time.

The first symptoms of a gout or rheumatic disease include an increase in temperature of the affected joint as well as swelling of the joint beyond the normal size. If these symptoms are recognised at an early stage, it is possible to initiate therapy at an equally early stage. Thus, drug therapies can then be initiated, especially with pain-relieving and anti-inflammatory drugs. Due to the clear risks and possible side effects, however, an individual assessment and indication of possible risks must be made in each case, especially in the case of a long-term prescription.

In the scientific research of such diseases of the joints as gout and rheumatoid arthritis, considerations have been made to what extent the course of the disease can be recorded by determining the temperature profiles of the sufferers at the affected joints. However, no device is known in the prior art that can be used to reliably record the course of temperature, especially of the affected joints, in a simple and convenient way for the patient.

From DE 29715113U1, similar to U.S. Pat. No. 6,846,106 B1, a finger temperature indicator ring is known, which is supposed to determine the body temperature reliably and independently of the patient's mental mood. This ring is worn like a normal ring between the joints of, for example, the ring finger. With this device, the finger temperature is measured directly next to the ring body and thus as inconspicuously as possible in order to exclude fluctuations in body temperature due to psychological stress. Measurement of the joint temperature or other parameters is not provided for in accordance with this publication.

In the state of the art, a number of devices are known that are designed to determine physiological parameters on the finger or other human limbs.

For example, DE 20 2006 009 103 describes a glove-like biological measuring device consisting of a glove-like main body that can be put on by the user and has electrical connections, wherein an opening is provided in the place of a finger where a biological measuring device can be placed. As such a biological measuring device, a light transmitter and a light receiver are proposed, which serve to measure the oxygen content in the blood.

EP 2437039A2 describes an ergonomic thermometer that is held in the hand and is intended for determining temperature of the skin surface. The disadvantage of this device is the need to carry the thermometer constantly under pressure between the fingers.

EP 3075312B1 discloses a ring-shaped device for measuring the patient's skin resistance, whereby the user's skin resistance is measured between an inner electrode and an outer electrode.

WO 2018/073827A1 discloses a device and system for recording physiological signals from a finger, the device being a body with a thimble-like tip attached to a finger by means of a band and intended to determine physiological conditions such as oxygen saturation of the blood.

All the above devices have in common that they are not suitable for measuring the temperature at a joint of a finger or a toe.

There is therefore a need for a device with which the temperature curve at a joint of a finger or toe can be reliably and safely determined over a longer period of time, thus opening up the possibility of initiating therapy, in particular the reduction of the patient's pain sensation, in such a way that the patient can be treated with lower doses of the therapeutic agents and thus a reduction in the long-term damage of the drug therapy is achieved.

On the part of the inventor of the present invention, a device has therefore been developed with which the temperature of one or more joints can be reliably and continuously measured in a manner that is simple and convenient, in particular for the patient, without the patient being subject to particular restrictions with regard to his mobility.

In a further development of the device according to the invention, the temperature course of several joints on one or more fingers, and/or toes, can be recorded. According to a further development, it is also possible to determine the increase in finger thickness due to swelling.

The present invention is therefore directed to a device for determining the temperature of a joint of a human hand or toe in the form of a ring-shaped sensor system.

Thus, the present invention relates to a sensor device for determining vital parameters relevant to inflammation, having a base body with a substantially rectangular base surface, an ring-shaped holder fixed to the base body for placing on a finger of a patient and at least one sensor arm fixed to the base body, wherein a sensor surface functionally associated with a temperature sensor is arranged at the end on the sensor arm and the sensor arm has a length such that the sensor surface comes to rest on the base joint of the patient's finger in the position of use, and wherein means are provided in the base body for storing and optionally transmitting the data measured by the temperature sensor to a data evaluation unit.

In its simplest form, the sensor device according to the invention consists of a base body with a ring-shaped holder attached to it. The base body, which is designed to accommodate the electronic components such as data memory, transmitting and receiving device, lithium-ion battery, etc., can essentially have the shape of a cuboid with a base surface and cover surface each curved in a part-circle shape, in which the electronic components are integrated accordingly. The at least one sensor arm is preferably arranged on the side of the base body facing the base joint of the finger and its length is such that the sensor element in the form of a temperature sensor arranged at the end of the sensor arm comes into contact with the base joint of the finger via the sensor surface. Depending on the design of the device according to the invention, the sensor arm can be a rigid arm or can be displaceable between an initial and an end position in the manner of a telescopic rod, so that the length can be adjusted according to the physiognomic conditions of the finger. The same applies to the second sensor arm provided in a further embodiment, which is arranged in the direction of the finger joint. Preferably, two ring elements, such as half rings, are arranged on the longitudinal sides of the basic body, which enclose the finger. Preferably, the ring segments/half rings are matched in width to the width of the longitudinal side of the basic body and the two circumferential edges of the ring-shaped holder are bevelled in the direction of the finger middle joint. In this way, the width of the long side of the base body is approximately maintained and a tilt-free fit of the sensor device on the finger is ensured.

In these ring segments, additional temperature sensors can preferably be arranged on the inner side resting on the skin of the finger in order to increase the number of measuring points on the finger and thus to be able to derive more precise diagnoses or data-based recommendations for action with an enlarged database. The measuring points in the ring segments are preferably placed along the radial mirror plane between the sensor arms aligned with the joint. Alternatively, they can also be arranged symmetrically between the sensor arms or in further possibly user-specific areas in the ring segments. The number of measuring points in the ring segments can be designed according to the application.

The material of the sensor device according to the invention is not decisive as long as the functioning of the device is not impaired. Particularly advantageously, the individual components can be made of plastic by 3D printing or by injection moulding. The sensor device according to the invention may also be integrated into a glove, which may facilitate usability for some patients. The sensor device according to the invention may be integrated into a waterproof and dustproof housing in which the electronic components for detection, storage, evaluation and data communication are protected from water and dust. Alternatively, water- and dust-proof encapsulated electronics may be used, which then also allows the use of a non-water-proof housing.

In one embodiment of the sensor device according to the invention, the at least one sensor arm arranged on the base body is preferably detachably fixed to the base body via an intermediate element. The intermediate element can be in the form of a flexible element which counteracts a deflection from the initial position with a restoring force, for example in the manner of a flexible washer. The intermediate element can also be detachably attached to the base body and/or the base body to the intermediate element. This enables sensor arms of different lengths and intermediate elements of different thicknesses to be fixed to a base body and adapted to the physiognomic conditions of the patient, such as finger or toe phalanx length.

With the help of the intermediate element, it can be achieved that the sensor element is in contact with the respective joint via the sensor surface even when the finger moves, whereby the restoring force of the intermediate element, e.g. as a spring element, ensures this. Furthermore, the intermediate element in the form of an arm spring element can be used to adjust the contact pressure of the sensor surface on the contact surface of the respective finger or toe joint. By using very flexible materials in the arm spring element, the above-mentioned contact pressure can also be increased, or by using very stiff materials in the arm spring element, the contact pressure can be reduced. Thus, an individual patient-specific adjustment of the contact pressure of the surface of the sensor arm in the direction of movement orthogonal to the contact surface of the sensor can be made.

In another embodiment, a further sensor arm can optionally be detachably fixed to the base body via an intermediate element in such a way that a sensor surface functionally assigned to a temperature sensor is arranged at the end of the sensor arm in such a way and the sensor arm has such a length that the sensor surface comes to rest on the patient's finger joint in the position of use. The intermediate element can be designed as an arm spring element like the previously described intermediate element. In the sensor device according to the invention, the sensor arm at the finger base joint and/or the sensor arm at the finger middle joint enclose an angle of 0° to 45°, in particular 20° to 30°—hereinafter referred to as the angle of incidence—with respect to the plane spanned by the base surface of the base body in the direction of the ring-shaped holder 2.

In a further embodiment of the sensor device according to the invention, a servomotor provided in the base body can be used to change the angle of incidence. If the sensor device according to the invention has two opposing sensor arms, two servomotors with one servomotor per sensor arm can be installed. This servomotor or these servomotors can change the aforementioned angle of incidence on one side or on both sides before, during or after the temperature measurement cycle of the sensor device according to the invention. This change of angle can allow a more comfortable mounting and removal of the sensor device according to the invention, furthermore also allow a change of the contact pressure of the sensor surface on the contact surface of the respective finger or toe joint. For this purpose, the angle of incidence mentioned above can also have negative values, so that one or both sensor arms point away from the centre axis of the ring-shaped holder.

In particular, for use of the sensor device according to the invention on a toe, the angle of incidence can have permanently negative values, so that the device is more comfortable to wear, e.g. in a measurement cycle lasting several hours, e.g. overnight.

Furthermore, the adjustment of the angle of incidence can be used to increase the contact force of the sensor surface on the contact surface of the respective finger or toe joint to such an extent that the patient is brought to a pain threshold that is no longer bearable for him. This allows the pressure pain sensitivity of the contact surface to be determined. A high sensitivity to pressure pain usually correlates with a high probability of rheumatoid arthritis. This adjustment of the angle of incidence with an increase in contact pressure can be carried out on one or both sensor arms at the same time or with a time delay.

The angular arrangement of the sensor arm(s) further supports the contact of the sensor surface with the respective joint and utilises the restoring force of the arm spring elements.

In a further embodiment, the ring-shaped holder can comprise two ring segments, at least one of which is fixed to the base body via a spring element.

In this embodiment, fitting the ring-shaped holder onto the finger is facilitated because the two ring segments, for example one mounted via a hinge, can move against each other.

The ring segments can be detachably fixed to the spring elements or together with them to the base body. Such an embodiment makes it possible to fix pairs of ring segments with different diameters to one embodiment of a base body and thus to provide the sensor device according to the invention in different size variants adapted to the patient. In this way, all rings can be constructed with only a few, possibly only one base body size variant.

The ring-shaped holder can comprise two ring segments, each of which is fixed to the base body via a spring element and forms a gap at the end opposite the base body, whereby the ring segments each have an electrode at their end facing the gap, to which an electrical voltage can be applied to form an electrical potential. This embodiment can be used to measure the finger thickness during a rheumatoid relapse and/or during a relapse prognosis measurement in everyday life, in addition to measuring the temperature of the finger base joint and/or finger middle joint. With increasing inflammation, the finger swells and the ends of the ring segments opposite the base body are pressed apart. As a result of the increase in the distance between the electrodes, the capacitance of the capacitor decreases and correlates with the increase in finger thickness. In this way, the therapist can get a more comprehensive picture of the patient's state of inflammation.

Furthermore, in another embodiment, the finger thickness can be determined, in addition to measuring the temperature of the finger base joint and/or finger middle joint, by a surface within the base body that is rigidly connected to a ring segment forming an angle with a rigid surface of the base body, which angle changes by the same amount (but opposite sign) as the angle of the ring segment, according to an auxiliary angle of the geometry theory. This angle is defined as the auxiliary angle. Since the auxiliary angle correlates negatively (=decreases) with the increase in finger thickness, the therapist can also get a comprehensive picture of the patient's state of inflammation from this.

The sensor device according to the invention can preferably have, on the side facing the finger or toe, in the ring-shaped holder consisting of the ring segments and the base body, at least one further sensor for determining a physiological parameter selected from conductivity of the skin, oxygen saturation of the blood, pulse and heart rhythm, concentration of erythrocytes, leucocytes of lymphocytes and haemoglobin (Hb).

The sensor device according to the invention can have a further device in the ring-shaped holder or the base body, via which measuring strips for analysing applied blood drops can be at least partially inserted. This allows disease-relevant inflammatory proteins, antibodies, uric acid, pathogens or other blood values to be determined, so that the patient's state of health can be further recorded and the presence of rheumatoid arthritis can also be further determined. Typical inflammatory values could also be determined in this way, among others: C-reactive protein (CRP), typical antibodies including antibodies against cyclic citrullinated peptides (anti-CCP) and rheumatoid factor (RF), as well as typical organic values such as alanine aminotransferase (ALT), aspartate aminotransferase (AST) and creatinine (Krea).

The sensor device according to the invention can have one or more further temperature sensors on the side facing away from the finger or toe during use, on the outer surface of the base body or the ring-shaped holder. These can be used to measure the temperature of the surrounding medium, which can be, for example, air but also water. Thus, the sensor device according to the invention can transmit the temperature back to the evaluation unit via sensors on the outer surfaces, so that a suitable starting temperature of the surrounding medium for a measuring cycle can be determined and the start of a measuring cycle can be enabled. This is very useful for a so-called cold provocation test, since fingers or toes are cooled down to a defined temperature, so that their self-warming allows a temperature warm-up curve to be recorded, which can be used to determine the prognosis and diagnosis of a rheumatoid disease process.

In addition to the determination of the temperature of the finger joint(s) and the determination of the finger thickness, further sensors can be arranged in the ring-shaped holder and/or the base body for the determination of further physiological parameters. In this way, the therapist can get an even more detailed picture of the patient's condition.

In addition to direct physiological parameters, the sensor device according to the invention can have an integrated gyroscope and/or an integrated acceleration sensor. By means of one or both sensors, information about the stiffness or mobility of the finger or toe can be obtained.

In addition, the invention also relates to a system for determining vital parameters relevant to inflammation, which comprises at least two sensor devices that are coupled to each other in a communication link for transmitting the data obtained and stored by the respective sensor device. With the aid of this coupled system, it is possible to determine the physiological parameters such as temperature, finger thickness, etc. on several fingers and to compare the measured values with each other.

In addition to two coupled sensor systems on two fingers, the invention also relates to a system of two coupled sensor devices on the same finger, which can be connected and coupled at the respective end faces of the respective facing sensor arm. The two sensor devices can then be connected via the middle phalanx joint, so that the ring-shaped holder of the primary system encloses the base phalanx (first finger phalanx) and the ring-shaped holder of the secondary system encloses the middle phalanx (second phalanx). This allows the sensor arm of the secondary system, which is directed towards the end of the finger, to come to rest on the finger end joint in the same way as described above, with adjustment of the contact force, etc.

Additional temperature sensors can preferably be arranged in the ring segments of the two coupled sensor devices, similar to the single sensor device, in order to increase the number of measuring points on the finger and thus to be able to derive more precise diagnoses or data-based recommendations for action with an increased data basis.

In coupled sensor devices according to the invention, the at least two sensor devices can be designed in such a way that one sensor device is the main device to which the second sensor device transmits the measurement data for storage and transmission to an evaluation unit. In this way, a more coordinated transmission of the measurement data to the evaluation unit is possible.

Furthermore, the coupling of the sensor device with an extension module (back of hand module) for measuring the temperature at various points on the back of the hand is also in accordance with the invention in a further development of the sensor device according to the invention. The sensor device can be coupled to the back of the hand module via the sensor arm arranged on the base joint of the finger. The back of the hand module can come into contact with an area with distributed temperature sensors on the back of the hand in order to provide a number of measuring points on the back of the hand and thus to allow more precise diagnoses or data-based recommendations for action with an enlarged database.

In addition to the above-mentioned coupling of two or more sensor devices according to the invention, a combination of one or more sensor devices according to the invention with a device for digital measurement of the hand force is also possible, which can be connected to one of the sensor devices with a cable or wireless data transmission. In several embodiments, this device may be designed as follows:

In the form of two spread force transducers, each of which is rotatably mounted at its end on a common pivot point. One force transducer is arranged with its outer surface resting on the palm of the hand, while the other force transducer is arranged with its outer surface resting on the inner surface of the fingers. At the above-mentioned pivot point, a restoring moment acts against the hand force, i.e. the force applied by the fingers in the direction of the palm. The restoring moment pushes the force transducers apart, while the hand force moves the force transducers together. Through this device, the force in the hands-more precisely the cumulative bending force of the fingers in the direction of the palm—can be measured;

In the form of a hollow volume which is provided with an internal pressure. A pressure sensor measures the internal pressure of the volume body at defined time intervals. A volumetric flow meter measures the volumetric flow at a nozzle attached directly to the volumetric body at defined time intervals. After the volumetric body has been filled by a hand pump, the patient is asked to squeeze the device as quickly and as firmly as possible to measure the hand force. Through this device, the force in the hands-more precisely the cumulative bending force of the fingers in the direction of the palm can be measured.

In the form of a tubular body with strain gauges which are attached to a finger or toe. Strain gauges are preferably attached to the outside of the tubular body at regular intervals in the longitudinal direction, which can measure a strain of the tube in the axial direction and provide information on the normal stresses in the material of the tubular body. The elongation of the strain gauges is caused by a bending of the measuring finger insofar as the increase in angle in the stretching process results in an elongation of the surface above the finger joint with the same radius. This device can be used to measure the force and/or the range of motion of the finger or toe over which the tubular body was previously placed. The tubular body can be permeable to air and water as well as impermeable to air and water.

All three embodiments of this device can be used in a combination evaluation of the hand force measuring device or mobility measuring device to determine a so-called morning stiffness of the fingers or an illness-related lack of strength. The parameters of the hand force measuring device could support the therapy recommendations, diagnoses and prognoses of the device according to the invention as a further data source to the temperature and threshold values of the finger (joints) from the device according to the invention.

In addition to the above-mentioned coupling of two or more sensor devices according to the invention, a combination of one or more sensor devices according to the invention with a device for the general measurement of the patient's/ wearer's body temperature similar to a fever measuring device or with a palm temperature measuring device is also possible. This measuring device can be connected to one of the sensor devices via a cable or wireless data transmission and can evaluate the measured values. In a joint evaluation, the measured values from body temperature measuring devices can be used to determine the general state of the immune system. This is important because a disturbance of the immune system as the cause of rheumatoid arthritis can lead to an overshooting of the immune reactions, which can usually manifest itself in fever and sweating. The measured values of the body temperature measuring device can thus support the therapy recommendations, diagnoses and prognoses of the device according to the invention as further data sources in addition to the temperature and threshold values of the finger (joints) of the device according to the invention.

Furthermore, the invention also relates to a kit for determining and evaluating vital parameters relevant to inflammation, which comprises at least one sensor device and a unit which is designed for evaluating and storing the data obtained and stored by the sensor device and preferably for preparing a therapy recommendation, wherein the at least one sensor unit and the evaluation unit are coupled to one another in a communication link. The kit according to the invention thus enables the therapist to initiate measures against the inflammatory state and thus to treat the rheumatic attacks and diagnose rheumatoid arthritis or gout, etc., at an early stage.

An exemplary embodiment of the device according to the invention is explained in detail below with reference to the schematic drawings. This shows:

FIG. 1 shows a first embodiment of the device according to the invention in side view;

FIG. 2A a cross-sectional view along the plane A-A through the device shown in FIG. 1;

FIG. 2B a detailed view of the detailed view C circled in FIG. 1;

FIG. 2C a detailed view B circled in FIG. 2A;

FIG. 3 a top view of the device according to the invention as shown in FIG. 1;

FIG. 4 a view of the device according to the invention as shown in FIG. 1 from below;

Figure 3:
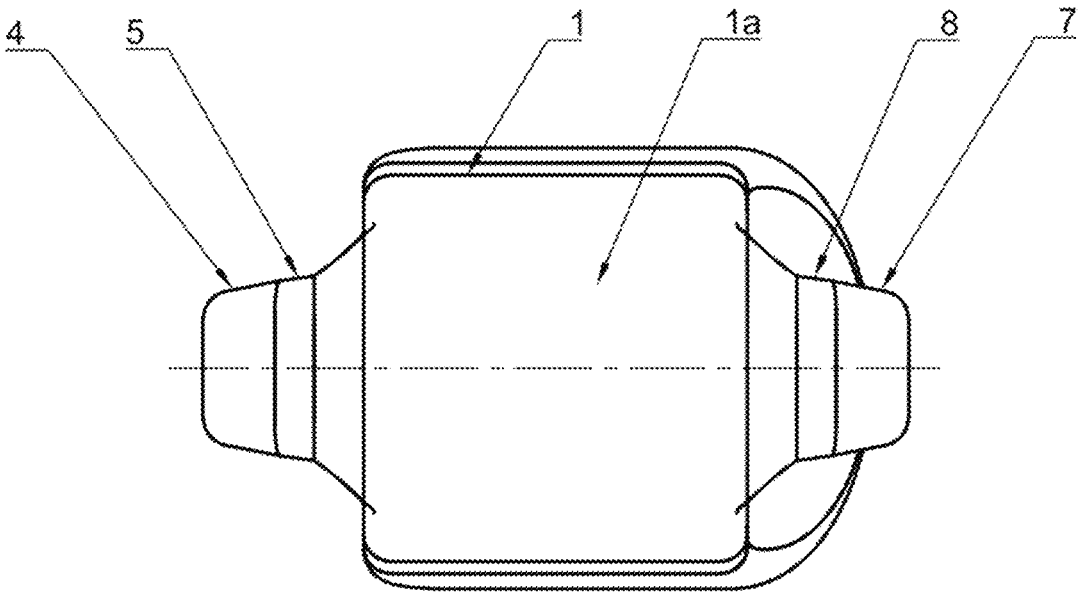

FIG. 8A-C a device according to the invention with two coupled sensor devices in a side view, in a schematic view of the arrangement on the finger and in a top view from above;

FIG. 9A-C a sensor device system according to the invention with two sensor devices coupled to each other and a back-of-hand module coupled thereto in a top view from below, in a side view and in a perspective top view; and FIG. 10A-C a device according to the invention with temperature sensors arranged in the ring segments in a top view, in a cross-sectional view along the line G_G indicated in FIG. 10 A, in a perspective top view from below.

As shown in FIG. 1, the sensor device 1 according to the invention in the embodiment shown comprises a base body 1A with ring segments/half rings 2A, 2B attached to it on both sides, at least one of which is connected to the base body 1A via a flexible intermediate element 3 as a spring element.

In one embodiment of the sensor device 1 according to the invention, half-rings (2A, 2B) are attached on both sides of the base body 1A via the intermediate elements as spring elements 3 (3A, 3B). The spring elements 3 are designed in such a way that the device 1 according to the invention, when mounted on the finger, rests with the half-rings 2A, 2B on the finger on both sides and forms the gap 12. The half-rings 2A, 2B are dimensioned in the radius of the surfaces of the hollow half-cylinder in such a way or can be designed in such a way, that a design of the sensor device according to the invention adapted to the respective finger diameter of the wearer is possible. The half-rings 2A, 2B are each chamfered at the front edge 10 facing the base joint of the finger in the position of use in the direction of the side opposite the base body 1A towards the half-ring ends 13 and 14 in such a way that, when the sensor device 1 according to the invention is placed on the finger in the position of use, the temperature sensor 6, which is fixed to the base body 1 on the sensor arm 4 via the intermediate element 5, comes to rest on the base joint of the finger. The sensor arm 4 and/or the intermediate element 5 is preferably designed in such a way that it is adapted to the length of the finger limb or is adjustable in length in the direction of the finger limb towards the base joint in the position of use in the manner of a telescope, taking into account the length of the patient's finger limb. In addition to the design of the intermediate element 5 in such a way that the temperature measuring surface of the temperature sensor 6 rests on the base joint of the finger, additional components not shown in the figure may be present on the sensor arm 4 which at least partially surround the finger and ensure a secure contact pressure for the temperature measuring surface of the temperature sensor 6 on the base joint of the finger or support it. On the side of each half-ring 2A, 2B facing away from the finger base joint in the position of use, each half-ring 2A, 2B can have a bevelled rear edge 11 which is bevelled in the direction of the finger centre joint in the position of use. Due to the axial length of each half ring being increased in this way, a reliable and tilt-free fit of the sensor device 1 on the finger is ensured in the position of use. On the side of the base body 1A of the sensor device 1 facing away from the base joint of the finger in the position of use, a sensor arm 7 can be provided similar to the side facing the base joint of the finger in the position of use, which is connected to the base body via an intermediate element 8 and has at least one temperature sensor 9 on its side facing the middle joint of the finger, which comes into contact with the middle joint of the finger in the position of use. The sensor arm 7 and/or the intermediate element 8 are dimensioned in terms of axial length or can be designed in a telescopic manner in such a way that secure contact of the temperature sensor 9 on the finger middle joint is made possible.

In the base body 1A, means are provided for storing and transmitting the data measured by the temperature sensor(s) to a data evaluation unit not shown in the figures, the temperature sensors being in communicative connection with the means for storage via one or more connections, for example cable connections. The data transmission to the evaluation unit can take place via a cable connection not shown in the drawing or wirelessly. A wireless transmission is advantageously offered via an NFC connection or a Bluetooth connection. For the power supply of the elements for temperature measurement, data storage and data transmission, a battery such as a lithium-ion battery adapted to the half-cylinder shape can be integrated in the base body 1. All interfaces for a possible above-mentioned cable connection are provided with a blind plug adapted to the interface contour, which is intended to counteract the penetration of dirt and water into the base body.

As shown in FIGS. 2A-2C, the half rings 2A and 2B are spaced apart by a gap 12 at the lower half ring edges 13 and 14 opposite the main body. As shown in FIG. 2B, a surface 15, 16 of a conductive metal separated by the gap 12 can be integrated into each of the half-ring lower edges 13 and 14, to which voltage is applied and forms a kind of capacitor. When the gap 12 is increased, a change in potential is produced on the metal surfaces 15 and 16 in the manner of a capacitor, which makes it possible to calculate the increase in the gap and thus the increase in finger thickness.

As shown in FIG. 2C in a magnified view, the base body can have an intermediate element 8 as well as the sensor arm 7 and the sensor element 9 facing the finger joint, which comes to rest on the finger joint in the position of use.

FIG. 3 shows a top view of the sensor device 1 according to the invention. The sensor arm 4 is connected to the base body 1A via the intermediate element 5. On the side of the base body opposite the finger base joint in the use position, which faces the finger middle joint in the use position, the sensor arm 7 is connected to the base body 1A via the arm spring element 8.

Figure 4:
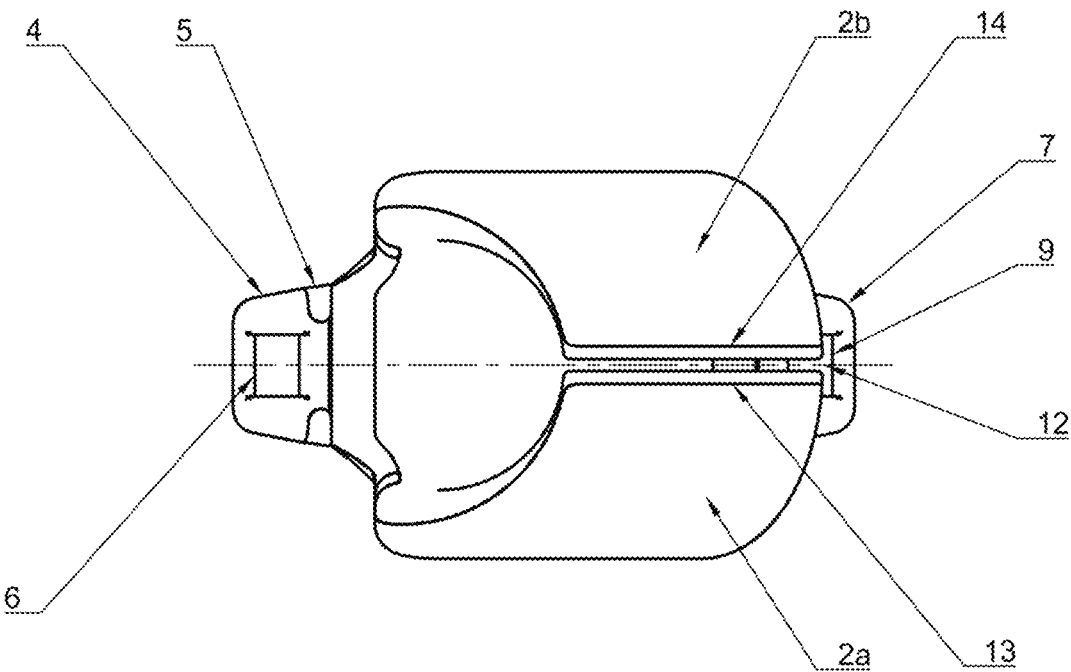

FIG. 4 shows a top view of the device according to the invention from below. The half-rings 2A and 2B are spaced apart from each other at their lower edges 13 and 14 opposite the base body via the gap 12. The sensor arm 4, which is arranged on the base body via the intermediate element 5, has a temperature sensor 6 facing the finger in the state of use. In a corresponding manner, the sensor arm 7, which is fixed to the base body via the intermediate element not shown in the drawing, has the temperature sensor 9, which rests on the finger joint in the position of use.

According to the invention, when the intermediate element is designed as a spring element 3, 5, 8, it is generally made of a flexible plastic, metal or non-metal, in which a restoring force acts against a deflection from the normal position, even under a basic pretension, so as to resume the normal position. In this way, it is achieved that the sensor arm and the temperature sensor arranged thereon rest on the joint in the position of use, in particular also during movement of the finger, and are pressed against the joint depending on the basic pretension. Similarly, the half-rings rest on the phalanx under the action of the at least one intermediate element in the form of an arm spring element in such a way that a reliable fit of the device according to the invention on the phalanx is ensured and at the same time further physiological parameters can be determined. For this purpose, further sensors can be arranged in the half-rings, which can be used, for example, to determine the conductivity of the skin, the oxygen saturation of the blood and further parameters such as pulse and heart rhythm, the concentration of erythrocytes, the concentration of leukocytes, the concentration of lymphocytes and the concentration of haemoglobin (Hb).

Figure 5:
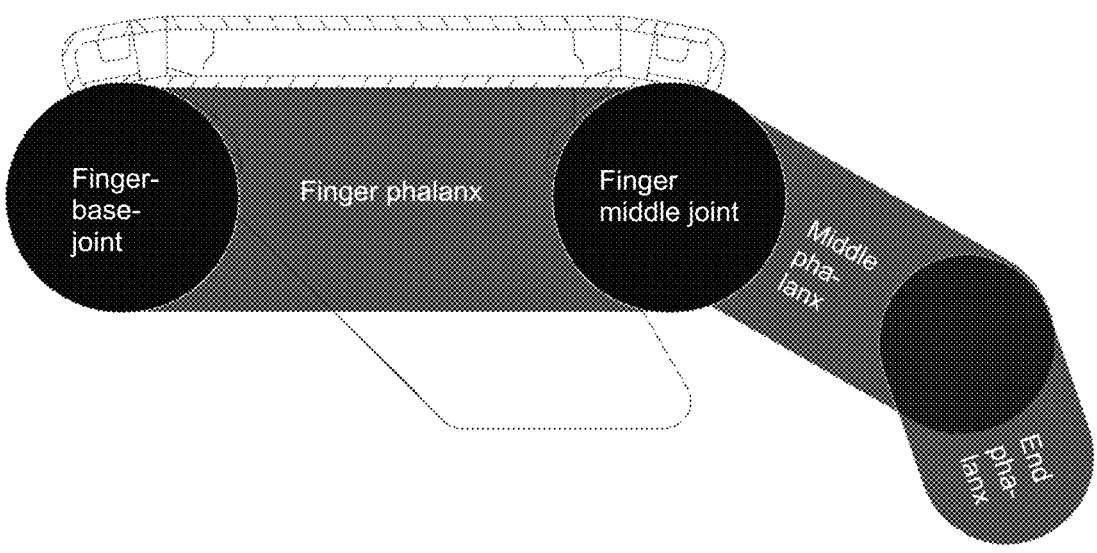
FIG. 5 is a schematic representation of the device according to the invention as shown in FIG. 1, attached to a finger.

FIG. 5 schematically shows the arrangement of the device according to the invention on a finger. A device according to the invention is attached to the finger in such a way that the temperature sensors rest on the base joint of the finger or on the middle joint of the finger.

In this way, a safe and optional differential temperature measurement can be carried out on both joints and the measurement data can be transmitted to an evaluation unit for evaluation. At the same time, in the event of a rheumatic episode or for the prognosis of a rheumatic episode, the increase in finger thickness can be determined via the half-rings 13 and 14 and their gap distance.

Figure 6:
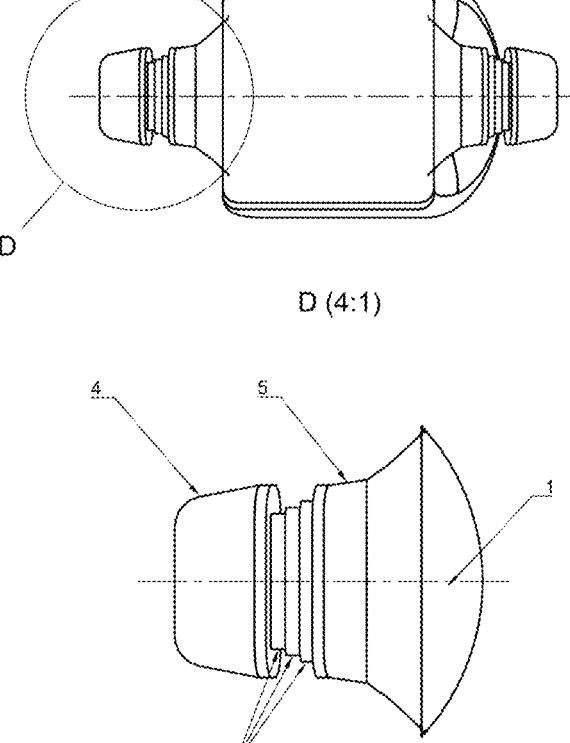
FIG. 6 shows a further embodiment of the device according to the invention with telescopic intermediate elements, optionally designed as spring elements.

FIG. 6 shows an embodiment of the device according to the invention, in which the sensor arms 4 and 7 are detachably fixed to the base body via an intermediate element 5 and 8 with telescopic links 17, which allow the sensor arm length to be adapted to the physiognomic conditions of the patient.

Figure 7:
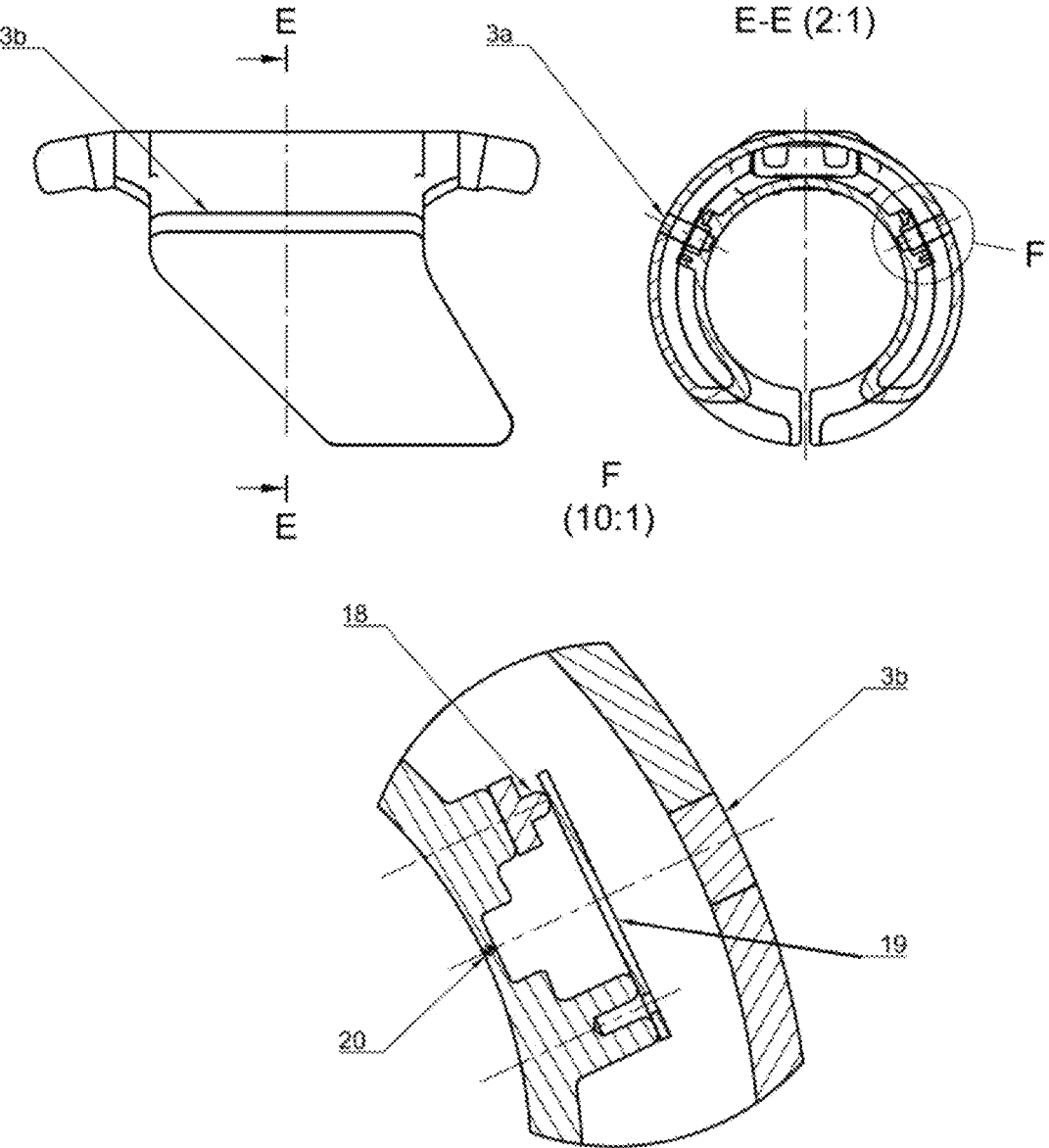
FIG. 7 shows a further embodiment of the device according to the invention for measuring the change in finger thickness.

FIG. 7 shows another embodiment for measuring the deflection of the spring element(s) with a side view of the sensor device according to the invention, a sectional view along the plane E-E as well as a detailed view F. In this embodiment, a force transducer/force sensor 18 measures a force applied to it by a bending rod/bending plate 19. This arrangement corresponds to that of a beam clamped on one side. The transverse deflection of the beam is proportional to the force measured at the contact surface on the force transducer (18). The transverse deflection is also proportional to the deflection of the spring element (3A/3B). In the force transducer 18, piezo elements convert the force into a voltage change, which is processed via an analogue-digital converter. The force is determined from the voltage change and from this the change in finger thickness.

FIGS. 8A-C show a device according to the invention with two coupled sensor devices (1;20) in a perspective top view, in a schematic view of the arrangement on the finger and in a top view from above. In the devices according to the invention, which concern at least one sensor unit such as the sensor devices (1;20) on the finger and/or a back of the hand module, the transitions between the components can be telescopically designed similar to the intermediate elements (5), so that a length adaptation of the transition areas of the sensor device according to the invention to different finger lengths and/or hand sizes is made possible.

FIGS. 9A-C show a sensor device system according to the invention with two sensor devices (1;20) coupled to each other and a back-of-hand module (21) coupled thereto with a fixing band (22) and sensors (23), for example temperature sensors or sensors for different parameters, in a top view from below, in a side view and in a perspective top view, in each case in a design for the left index finger. In versions for other fingers, the shape of the back of the hand module (21) can be adapted accordingly.

FIGS. 10A-C show a sensor device (1) according to the invention with sensors (23), for example temperature sensors, arranged in the ring segments (2A;2B) in a top view from above, in a cross-sectional view along the line G_G indicated in FIG. 10A, and in a perspective top view from below.

LIST OF REFERENCE SIGNS

1 Sensor device
1A Base body
2 Ring-shaped holder (2) with ring segment (2A, 2B)

3 Spring element (3A, 3B)
4 Sensor arm
5 Intermediate element
6 Temperature sensor
7 Sensor arm
8 Intermediate element
9 Temperature sensor
10 Front edge
11 Trailing edge
12 Gap
13 Ring segment lower edge
14 Ring segment lower edge
15 Sensor surface
16 Sensor surface
17 Telescopic links
18 Force sensor
19 Bending rod
20 Sensor device middle link (analogue to Pos 1)
21 Back of the hand module
22 Fixation tape
23 Sensor

The invention claimed is:

1. Sensor device (1) for determining vital parameters relevant to inflammation, comprising:
   a base body (1a) with a substantially rectangular base surface,
   a ring-shaped holder (2), which is fixed to the base body (1a), for placing on a finger of a patient, and
   at least one sensor arm (4) detachably fixed to the base body (1a), wherein a sensor surface, which is functionally associated with a temperature sensor (6), is arranged at the end on the at least one sensor arm (4) and is configured to rest on the base joint of the patient's finger in use,
   wherein means for storing and optionally transmitting data measured by the temperature sensor to a data evaluation unit are provided in the base body, and
   wherein the at least one sensor arm (4) is detachably fixed to the base body via an intermediate element (5).

2. Sensor device (1) for determining vital parameters relevant to inflammation according to claim 1,
   wherein a further sensor arm (7) is detachably fixed to the base body (1a) so that a sensor surface functionally associated with a further temperature sensor (9) is arranged at the end of the further sensor arm (7) and is configured to rest on the patient's finger middle joint in the position of use.

3. Sensor device (1) for determining vital parameters relevant to inflammation according to claim 2, wherein the at least one sensor arm (4) and/or the further sensor arm (7) encloses an angle of 0° to 45°, in a direction of the ring-shaped holder (2) with respect to a plane spanned by the base surface of the base body (1a).

4. Sensor device (1) for determining vital parameters relevant to inflammation according to claim 2, wherein the further sensor arm (7) is detachably fixed to the base body via a further intermediate element (8).

5. Sensor device (1) for determining vital parameters relevant to inflammation according to claim 2, wherein the at least one sensor arm (4) and/or the further sensor arm (7) encloses an angle of 20° to 30° in a direction of the ring-shaped holder (2) with respect to a plane spanned by the base surface of the base body (1a).

6. Sensor device (1) for determining vital parameters relevant to inflammation according to claim 1, wherein the ring-shaped holder (2) comprises two ring segments (2A, 2B), at least one of which is fixed to the base body (1A) via a spring element (3).

7. Sensor device (1) for determining vital parameters relevant to inflammation according to claim 6, wherein the ring-shaped holder (2) comprises two ring segments (2A, 2B) which are each fixed to the base body (1A) via a spring element (3A, 3B) and form a gap (12) at the end opposite the base body (1A), the ring segments (2A, 2B) each having at least one sensor for determining the gap width at their end (13, 14) facing the gap (12).

8. Sensor device (1) for determining vital parameters relevant to inflammation according to claim 1, wherein at least one further sensor (23) for determining a physiological parameter comprising the conductivity of the skin, the oxygen saturation of the blood, the pulse, the heart rhythm, the concentration of blood cells or the concentration of haemoglobin (Hb) is arranged in the ring-shaped holder (2) or the base body (1A).

9. System for determining vital parameters relevant to inflammation, comprising:
   at least one sensor device (1) according to claim 1; and
   a back-of-hand module (21) with sensors (23) which are coupled to one another for transmitting the data obtained and stored by the respective sensor device in a communication link.

10. Kit for determining and evaluating vital parameters relevant to inflammation, comprising:
   at least one sensor device according to claim 1; and
   a unit for evaluating and storing the data obtained and stored by the sensor device,
   wherein the at least one sensor unit and the evaluation unit are coupled to one another in a communication link.

11. Sensor device (1) for determining vital parameters relevant to inflammation according to claim 1, wherein the at least one sensor arm (4) is detachably fixed to the base body via a flexible intermediate element (5).

12. System for determining vital parameters relevant to inflammation, comprising:
   at least two sensor devices (1) according to claim 1; and a back-of-hand module (21) with sensors (23) which are coupled to one another for transmitting the data obtained and stored by the respective sensor device in a communication link.

13. Kit for determining and evaluating vital parameters relevant to inflammation, comprising:
   at least one sensor device according to claim 1; and
   a unit for evaluating and storing the data obtained and stored by the sensor device and for preparing a therapy recommendation or a behavior recommendation for the patient,
   wherein the at least one sensor unit and the evaluation unit are coupled to one another in a communication link.

14. A sensor device for determining vital parameters relevant to inflammation, comprising:
   a base body having a substantially rectangular base surface;
   a ring-shaped holder fixed to the base body and configured to be placed on a finger of a patient;
   a first sensor arm detachably fixed to the base body via a first intermediate element; and
   a first temperature sensor having a sensor surface arranged at an end on the first sensor arm and configured to rest on a base joint of the patient's finger.

15. A sensor device according to claim 14, further comprising:
   a second sensor arm detachably fixed to the base body via a second intermediate element; and
   a second temperature sensor having a sensor surface arranged at the end of the second sensor arm and configured to rest on a middle joint of the patient's finger.

16. A sensor device according to claim 15, wherein the first intermediate element and the second intermediate element are telescopically adjustable.

17. A sensor device according to claim 14, wherein the ring-shaped holder comprises two opposing half-cylindrical ring segments, at least one of which is fixed to the base body via a spring element.

* * * * *